United States Patent [19]
Porter et al.

[11] Patent Number: 5,635,047
[45] Date of Patent: Jun. 3, 1997

[54] ELECTROCHEMICAL METHOD OF CONTROLLING THIOLATE COVERAGE ON A CONDUCTIVE SUBSTRATE SUCH AS GOLD

[75] Inventors: Marc D. Porter, Ames, Iowa; Duane E. Weisshaar, Sioux Falls, S. Dak.

[73] Assignee: Iowa State University Research Foundation, Inc., Ames, Iowa

[21] Appl. No.: 257,471

[22] Filed: Jun. 9, 1994

Related U.S. Application Data

[63] Continuation of Ser. No. 921,305, Jul. 28, 1992, abandoned.
[51] Int. Cl.$^6$ ................................. C25D 13/00
[52] U.S. Cl. ................. 204/421; 204/450; 204/489; 205/444; 205/445
[58] Field of Search .................. 205/317, 444, 205/445; 204/180.1, 180.2, 181.4, 72, 450, 471, 489

[56] References Cited

U.S. PATENT DOCUMENTS

| | | | |
|---|---|---|---|
| 4,940,516 | 7/1990 | Wegmann et al. | 205/317 |
| 4,964,972 | 10/1990 | Sagiv et al. | 204/418 |

OTHER PUBLICATIONS

Weisshaar et al; "Thermodynamically Controlled Electrochemical Formation of Thiolate Monolayers at Gold" J. Am. Chem. Soc., 114 (14), 1992 pp. 5860–5862.

*Primary Examiner*—Howard E. Schain
*Assistant Examiner*—C. Delacroix-Muirheid
*Attorney, Agent, or Firm*—Leydig, Voit & Mayer, Ltd.

[57] ABSTRACT

An electrochemical method for forming a partial monomolecular layer of a predetermined extent of coverage of a thiolate of the formula, $XRS^-$, wherein R can be a linear or branched chain hydrocarbon or an aromatic or the like and X can be any compatible end group, e.g., OH, COOH, $CH_3$ or the like, upon a substrate such as gold, which involves applying in an electrochemical system a constant voltage preselected to yield the desired predetermined extent of coverage.

14 Claims, 13 Drawing Sheets

ELECTROCHEMICAL METHOD OF CONTROLLING THIOLATE COVERAGE ON A CONDUCTIVE SUBSTRATE SUCH AS GOLD

GRANT REFERENCE

The United States government has certain rights in this invention pursuant to Contract No. W-7405-Eng-82 (DOE-ISU) and Contract No. ITA81-02 between the U.S. National Aeronautic and Space Administration and Iowa State University.

This application is a continuation of U.S. Ser. No. 07/921,305, filed Jul. 28, 1992, now abandoned.

FIELD OF THE INVENTION

This invention relates to thiolate monolayers and, more particularly, to a thermodynamically controlled electrochemical deposition of a thiolate on a substrate such as gold.

BACKGROUND OF THE INVENTION

The chemical derivatization of metal surfaces has been utilized as a means to control the interfacial reactivity of a metal in relation to processes such as adhesion, lubrication, corrosion, electrocatalysis, or electroanalysis. Understanding the factors that govern the formation of stable derivatization layers is accordingly of both technological and fundamental importance. For these reasons, monomolecular films formed from surfactant molecules possessing a head group that binds to a particular metal and a tail group that possesses a specific chemical functionality have been examined as model interfacial structures.

Thin film resonators have been, and are currently being, investigated as feedback elements in rf/microwave frequency oscillators. In general, the frequency of the resonator depends upon the mass attached to it. Thus, substrates having a thiolate monolayer thereon may find utility in thin film resonators. A thiolate is used that has an end group selected to bind selectively to a target analyte (e.g., an airborne pollutant or a solution species). When the coated resonator is exposed to an environment containing the target analyte, the analyte binds to the surface and changes the resonator frequency. The frequency change then can be correlated with the target analyte concentration in the environment. Arrays of resonators with a different end group in each element can produce a sensor for a wide range of target analytes. For example, possible applications include biomedical monitoring, industrial process monitoring, and applications for residential use (e.g.—a carbon monoxide detector coupled with a smoke detector).

Organosulfur surfactants are known to bind strongly at a variety of metals such as iron, copper, platinum, gold, and silver; and monolayer films of n-alkanethiolates on gold have been extensively studied as to their structure, electronic properties, and permeability to ion transport. In "Desorption of n-alkanethiol Monolayers from Polycrystalline Au and Ag Electrodes," *J. Electroanal. Chem. Interfacial Electrochem.*, 1991, 310, 335–59, Widrig, Chung and Porter used voltammetric techniques to characterize monolayers formed at Au and Ag surfaces by the spontaneous adsorption of n-alkanethiols and to examine the chemistry of the bound thiol head group. Electrode reactions corresponding to the oxidative- and reductive-desorption of the adsorbed n-alkanethiolate monolayers were discussed and described. The charge found for the reductive desorption of the n-alkanethiolate monolayer at Au was consistent with the electrode reaction

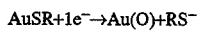

In the positive scan of the first voltage cycle, as described as page 345, Widrig et al. state that partial re-oxidation of the generated reduction product is apparent. It was hypothesized that the product may be either the original surface species or the corresponding dialkyl disulfide. Further, in the second cycle, it was stated that the re-oxidized material was reduced at voltages more positive than the voltage for reduction of the original surface species. When comparing voltammograms recorded at a given scan rate, the quantity of material re-oxidized, it is stated, was greater for monolayers of long-chain n-alkanethiolates because the reduced n-alkanethiolate is more likely to precipitate at the electrode surface. Reference is made to FIGS. 4B and 4C.

Widrig et al., as noted, formed the thiolate monolayer by spontaneous adsorption from ethanolic solutions. In general, the substrates were immersed in approximately 1 mM solutions of the n-alkanethiol for 2 to 24 hours, were emersed, rinsed with ethanol, and then allowed to dry.

Where control of the extent of coverage of the monomolecular layer is unimportant, self-assembly of the layer by spontaneous adsorption is generally satisfactory. Self-assembly of a monolayer in this fashion typically proceeds extremely rapidly, occurring in milliseconds or so, with many thiols. This is because the reaction is essentially diffusion controlled for many thiols, i.e., the thiol reacts as fast as it reaches the gold or other surface. For other thiols, the reaction is slower; and assembly times of minutes or hours are required.

Further, where a predetermined level of coverage is required, quite dilute solutions ($<10^{-5}$M) of the thiol have been used so as to attempt to slow the reaction kinetics down enough to provide the degree of control needed for the particular application. While providing some degree of control, this dilution approach is time-consuming and laborious. Reproducibility depends upon controlling the concentration of the thiol solution. The dilute solutions used cannot usually be measured directly so the solutions are made by serial dilution. Small variations in concentrations can have a significant effect on the assembly times. Also, diffusion rates are temperature dependent, so that reproducibility and precise deposition control also require appropriate temperature control.

Further, control of the composition of multicomponent layers is also an important consideration. While it is possible to put down a partial layer of one thiolate using a dilute solution and then complete the layer with another thiolate, this approach suffers from the limitations herein discussed.

Mixed layers can also be assembled from solutions of thiol mixtures. However, the composition on the surface is not the same as the composition in the solution. Also, both thermodynamics and kinetics determine the surface composition. Satisfactory control of composition with this approach is accordingly very difficult.

Both the dilute and mixed solutions approaches also require some kind of determination of the surface composition. This can be accomplished by using, for example, X-ray photoelectron spectroscopy or electrochemistry. Such an ancillary determination requires that the end groups of the thiolates involved have different chemistries.

In part, due to the difficulties in providing a facile technique for controlling the coverage of the thiolate, the use of this technology has been limited. Accordingly, a principal object of the present invention is to provide a facile method for thiolate deposition which is characterized by enhanced control of the location and amount of thiolate deposited on a substrate such as gold.

Yet another object of the present invention lies in the provision of a method that allows formation of a mixed thiolate layer of known composition without also requiring different end groups on the thiolates being utilized.

Other objects and advantages of the present invention will become apparent as the following description proceeds.

SUMMARY OF THE INVENTION

In accordance with this invention, it has been discovered that coverage of a thiolate at a substrate such as gold can be controlled by utilizing a thermodynamically controlled electrodeposition process. To this end, the extent of the coverage of the substrate is controlled by appropriate voltage control. In this fashion, controlled and predictable coverage is provided by a facile method which is applicable generally to the types of thiolate monolayers desired for the diverse applications involved.

DETAILED DESCRIPTION OF THE INVENTION

Figure 1:
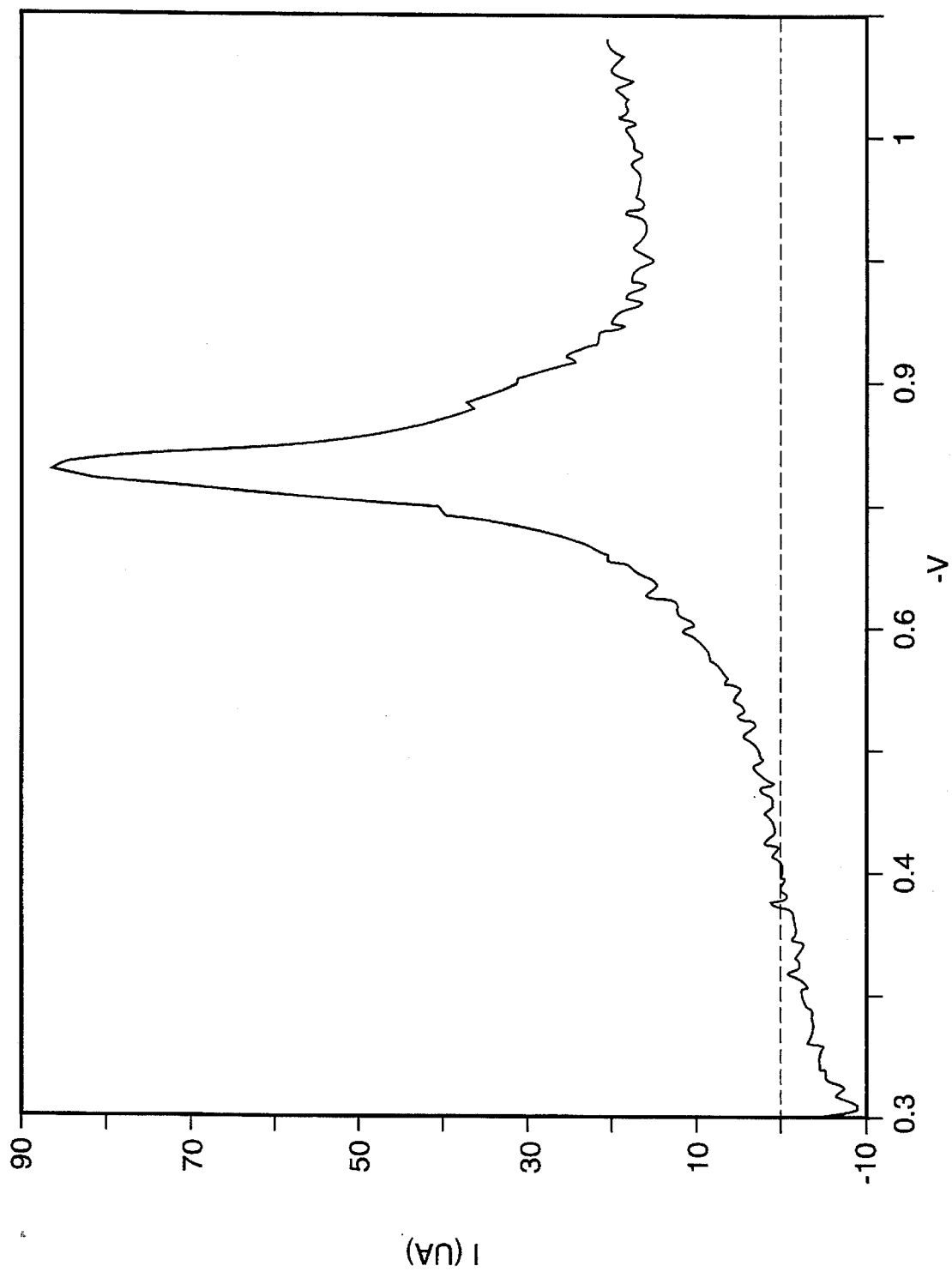
FIG. 1 is a voltammogram showing the reductive desorption of an $HOCH_2CH_2S^-$ thiolate monolayer that had been electrochemically deposited onto a substrate.

The compounds utilized to provide the controlled thiolate coverage are characterized by the general formula:

XRSY

In general, the XR moiety will determine the characteristics of the interface which relates to specific applications, S provides the attachment to the substrate, and Y is lost during deposition.

As to Y, Y may comprise any moiety that forms a weaker bond with sulfur in the XRSY molecule than the $S^-$ substrate bond attaching the $XRS^-$ moiety to the substrate surface. In addition, Y should be compatible with the voltages used in the deposition (viz.—any electrochemistry from Y must not interfere with the deposition), with the solvent and electrolyte employed, and with, of course, the X and R moieties employed.

Accordingly, Y can be H. In that event, XRSY is, of course, a thiol; and numerous thiols are commercially available. In addition, Y can comprise M, a metal, so that XRSY is a thiolate salt. In general, M may be virtually any metal, including the alkali metals (e.g.—Na, K) or alkaline earth metals (e.g.—Ca, Mg). Still further, Y can be a non-metal cation such as $N_4+$ or an organic group (another R group), so long as, of course, the requirements for the Y moiety are met.

With regard to R, the selection of the appropriate group will be dependent upon the characteristics desired for the interface for the specific application, i.e., the packing density of the molecules on the surface, the relative stability of the partial or full monolayer, the thickness of the film layer desired and control of the interaction between neighboring R groups on the surface. As with the Y group, the R moiety should be compatible with the voltages used in deposition, and with the solvent and electrolyte used. The R moiety should also be compatible with the X and Y groups employed.

As may be appreciated, the R moiety may be viewed as an isolation layer separating the $S^-$ moiety attached to the surface from its X end group. Innumerable moieties satisfy the requirements set forth herein and may be suitably utilized, depending, of course, upon the desired characteristics for the specific application.

Thus, in one embodiment, R can be a linear alkane chain, viz.—$(CH_2)_n$, wherein n is an integer of 1 or more. In general, as the length of the methylene chain increases, the packing density of the monolayer on the substrate surface also increases. It is believed that the packing density does not increase after the chain is increased to about $(CH_2)_{11}$ or $(CH_2)_{12}$. However, the permeability may well decrease with chains of increasing length. The practical limit for n is determined by the solubility of the long chain alkane in the solvent selected, i.e., the XRSY compound must be soluble in the solvent of choice in the amount necessary to provide the desired coverage. The choice of n is thus application dependent. Methylene chains of up to $(CH_2)_{15}$ have been used with satisfactory results.

In addition, the backbone of R (the portion of R that connects X to S) may be comprised of a variety of linkages besides linear alkyl chains. For example, R may be, or may include, aromatic rings (e.g.—phenyl, naphthyl), or it may include heteroatom linkages (e.g.—via oxygen in esters and ethers, via nitrogen in amides). There may also be substitution or branching on the backbone. The general formula for these substituted and branched compounds is $XR(CR'R'')_nSY$, where, in addition to being H as in the methylene chains, R' and R", which may be the same or different, can be almost any functional group including, for example, alkyl chain (branch), aromatic group, ester, ether, ketone, halogen, or amine; and n is an integer as previously discussed. Of course, the compatibility constraints discussed herein for R must be met.

As to the X end group, the particular selection will be determined by the specific application; and the possibilities are virtually limitless. In general, the principal requirements for X are the same as those previously discussed regarding R and Y. As illustrative examples, it has been found suitable to utilize, as X, $CH_3$, $CF_3(CF_2)_7$, COOH and OH. As additional illustrative examples, there can be named inorganic complexes with thiol ligands, and organometallic compounds. Cyclodextrins and crown ethers may also be used.

With regard to the electrochemical system utilized to provide the thiolate layer, any suitable voltammetric analyzer and cell assembly system could be used. When the solvent employed is water or ethanol, it has thus been found suitable to utilize a Ag/AgCl reference electrode isolated, if desired, by an aqueous KOH salt bridge. Any reference electrode compatible with the solvent and electrolyte may be utilized including pseudo-references such as platinum or silver wire. Platinum or any suitable conductor may be used as the counter (auxiliary) electrode.

The choice of the electrodes used follows the requirements known and employed for any other electrochemical technique. The particular system desired is a matter of choice, well within the level of skill in this field.

Any of a variety of liquids may be used as the solvent. Thus, it is suitable to use an aqueous solution. However, for better solubility, it has been found suitable to use ethanol. Another illustrative example of a suitable solvent is acetonitrile. Further, any solvent compatible with the requirements of the electrochemistry and with the thiol (or other XRSY compound employed) can be used.

The prime requirements for the electrolyte are compatibility with the solvent, the XRSY compound being utilized, and with the electrochemistry, as well as providing sufficient conductivity to support the appropriate current flow. The particular material employed as the electrolyte can, of course, vary depending upon the particular electrochemical system used. It has been found suitable to utilize KOH as the electrolyte. Where nonaqueous solvents are used, tetraalkylammonium salts are known in the art and are used extensively as electrolytes. Other suitable materials useful as electrolytes are also known in the art and may be employed.

The amount of electrolyte used is dependent upon the solubility in the solvent and the concentration needed to produce the required conductivity. Where water is the solvent, KOH, for example, can be employed in an amount of from 0.1M up to the limits of its solubility. Further, where water and ethanol are employed, it has been found suitable, and is preferred, to use KOH at a level of 0.4 to 0.5M.

In addition, the electrochemical system utilized must provide a voltage window at the negative voltages required for the electrodeposition reaction. The use of KOH as the electrolyte shifts the $H^+$ reduction wave to the more negative voltages necessary for the appropriate voltage window. The appropriate choice of solvent will also provide the necessary voltage window.

As to the level of the XRSY compound, this will be dictated by, in general, solubility and the composition of the compound. A typical range will be a concentration of about 1 mM up to about 10 mM. Concentrations lower than 1 mM could be used, but longer times would probably be required. At these lower concentrations, diffusion becomes an important process which can make control more difficult for the same reasons that coverage control by self-assembly from dilute solutions can be problematic, as previously discussed.

With respect to the substrate, gold, supported, if desired, on silicon, mica, glass or the like, is the preferred substrate. An adhesion promoter, such as a thin layer of chromium may be used between the support and the gold, as is known. Vapor deposition techniques for applying gold to the support, such as silicon, mica and the like, are known and are within the level of skill in this field. Such vapor deposition techniques produce, almost exclusively, the Au(111) plane. Having only one crystal face simplifies the electrochemistry. However, other techniques are known for providing gold-supported materials, and any of these may be utilized, as is desired. Indeed, gold may be used as the substrate without any support, if desired. When gold is to be used, the particular technique utilized and the supporting layer selected will be principally dictated by the particular application. Moreover, while gold is the preferred substrate, it should be appreciated that the method of this invention is likewise applicable to other conductive substrates, such as any metal to which the thiolate will oxidatively bind and is compatible with the electrochemistry. Illustrative examples include platinum, silver and copper.

In general, the procedure to prepare the electrochemical system for deposition is as follows. The desired concentration of the thiol (or other XRSY compound used) and electrolyte are dissolved in the chosen solvent. The solvent is then placed in the electrochemical cell. The working, reference and counter electrodes are then placed in the cell; and the solution is purged with an inert gas (e.g., nitrogen, argon or the like) for a time sufficient to remove any dissolved oxygen (e.g., about 5 to 10 minutes where water is the solvent and about 3 minutes when ethanol is used). As may be appreciated, the order of these steps is not critical.

The electrodes are then connected to an appropriate voltammetric analyzer. The applied voltage is first set at a voltage where any adsorbed compounds would be desorbed so as to completely clean the substrate (working electrode). This cleaning voltage is applied for an appropriate time, typically 10–30 seconds or so, preferably while stirring the solution (mechanically or bubbling with the purge gas) to facilitate transport of any desorbed impurities away from the substrate surface to prevent readsorption. The voltage is then stepped to the deposition voltage, which has been preselected from the anodic deposition wave, for an appropriate time to establish a redox equilibrium, thus providing for the desired level of coverage. For XRSY that spontaneously adsorb rapidly, a deposition time of a minute or so has proven to be sufficient time to establish the redox equilibrium. For XRSY that spontaneously adsorb at a slower rate, longer times will be required. After deposition, the working electrode is rinsed thoroughly while it is still in contact with the electrolyte solution and with the voltage still applied so as to prevent further deposition by self-assembly.

The sharp, symmetrical shape of the oxidative peaks that can be obtained using the surface deposition process of the present invention when alkanethiols are employed is indicative of a fast electron transfer rate at the appropriate voltammetric time scale, which, in turn, minimizes the time needed to establish coverage equilibrium at the chosen applied voltage. There is evidence suggesting that other thiols (other R or X) also exhibit electron transfer rates that are fast enough to achieve equilibrium with the applied voltage within a convenient time period.

In accordance with the present invention, the desired coverage of the thiolate is produced by the redox equilibrium established at the constant applied voltage. Thus, by the selection of the desired voltage for the particular system, the level of coverage of the monolayer that is deposited can be predetermined and controlled within reasonably close tolerances.

For example, when a hexanethiolate partial monolayer is formed using the illustrative and preferred embodiment described herein, the coverage for an applied constant voltage of $-0.89$ V corresponds to $4.0 \times 10^{-10}$ moles/cm$^2$, while constant applied voltages of $-0.90$ V and $-0.91$ V provide coverages, respectively, of $1.9 \times 10^{-10}$ and $0.80 \times 10^{-10}$ moles/cm$^2$.

For any particular system, establishing the particular voltages that translate to the desired surface coverage can be determined by straightforward experimental procedures. Thus, after deposition by the described procedure, but before removing the substrate from the solution, a negative linear voltage sweep is initiated at the applied voltage in order to desorb the partial thiolate monolayer just deposited. The charge under the desorption wave thus produced is used to calculate the coverage for that particular applied voltage. Repeating the voltage step sequence (cleaning, deposition), but not the linear sweep, produces a partial monolayer of the same coverage.

Contact angle and infrared reflection spectroscopic characterization of full thiolate monolayers establish the qualitative similarities of an electrodeposited monolayer in accordance with the present invention and those of a self-assembled thiolate monolayer (the self-assembled monolayer being obtained by conventional spontaneous adsorption techniques). Advancing contact angles ($\theta_a$) of hexadecane (HD) and water at the two monolayers are effectively identical, viz.—$\theta_a$ is 108° (for H$_2$O) and 44° (for HD) for the electrodeposited monolayer in accordance with the present invention in comparison with 107° and 44°, respectively, for the self-assembled thiolate monolayer. In addition, the absorbances and positions of the bands in the C–H stretching region of the infrared reflection spectra are comparable within what is considered preparative reproducibility. These similarities confirm that electrochemical deposition in accordance with the present invention produces a monolayer of the expected composition and spatial arrangement of a self-assembled monolayer, viz.—an average polymethylene chain tilt of about 30° from the surface normal.

The following Examples are illustrative of, but not in limitation of, the present invention. As to the common elements to these Examples, a Ag/AgCl/ saturated KCl reference electrode was used except in Examples 11 and 13 where a platinum wire pseudo-reference was used. An aqueous KOH salt bridge was used in all Examples except Examples 1–3, 11 and 13 where no bridge was used. A platinum counter electrode was used in all cases. The substrate utilized was clamped against an elastomer O-ring at the bottom of the cell. (Only the area inside the O-ring contacts solution, so moving the O-ring to another spot on the substrate gives, in effect, a new electrode.) The thiol used was then added to either ethanolic KOH, aqueous KOH, or aqueous LiOH, depending on the electrolyte chosen, and the resulting mixture was then added to the cell after which the reference and counter electrodes were immersed in the solution. In each Example, the electrolyte was present at 0.5M, while the thiol was present in an amount of 10 mM. All solutions were purged with nitrogen to remove dissolved oxygen; aqueous solutions for at least 5 minutes and ethanol solutions for at least 3 minutes. The scan rate for all voltage scans was 100 mV/s. The substrate in Examples 1 and 2 was a 300 nm layer of gold deposited on a 15 nm layer of chromium (used to enhance adhesion) on a single crystal wafer of silicon referred to henceforth as Au/Si. The gold and chromium layers were both formed by vapor deposition. The substrate in the remaining examples was a 300 nm layer of gold vapor deposited on a freshly cleaved 1 inch×3 inch sheet of green mica (no chromium was used) referred to henceforth as Au/mica.

EXAMPLE 1

This Example shows verification of the formation of a HOCH$_2$CH$_2$S$^-$ layer on Au/Si.

The solution added to the electrochemical apparatus was made by dispersing 10 mM mercaptoethanol in 0.5M LiOH in water. The voltage was set at $-1.10$ V so as to clean the substrate and was then stepped to $-0.20$ V for 1 second. Thereafter, a linear voltage scan from $-0.20$ V to $-1.10$ V was made.

The voltammogram thus produced is shown in FIG. 1. The peak between $-0.70$ V and $-0.80$ V shows the desorption of the thiolate layer that was deposited during the voltage step. This confirms that a monolayer had been adsorbed on the substrate. The step to $-0.20$ V is the voltage at which the thiolate was deposited.

EXAMPLE 2

This Example shows the reductive desorption and the oxidative adsorption of a HOCH$_2$CH$_2$S$^-$ thiolate layer in accordance with the present invention.

Figure 2:
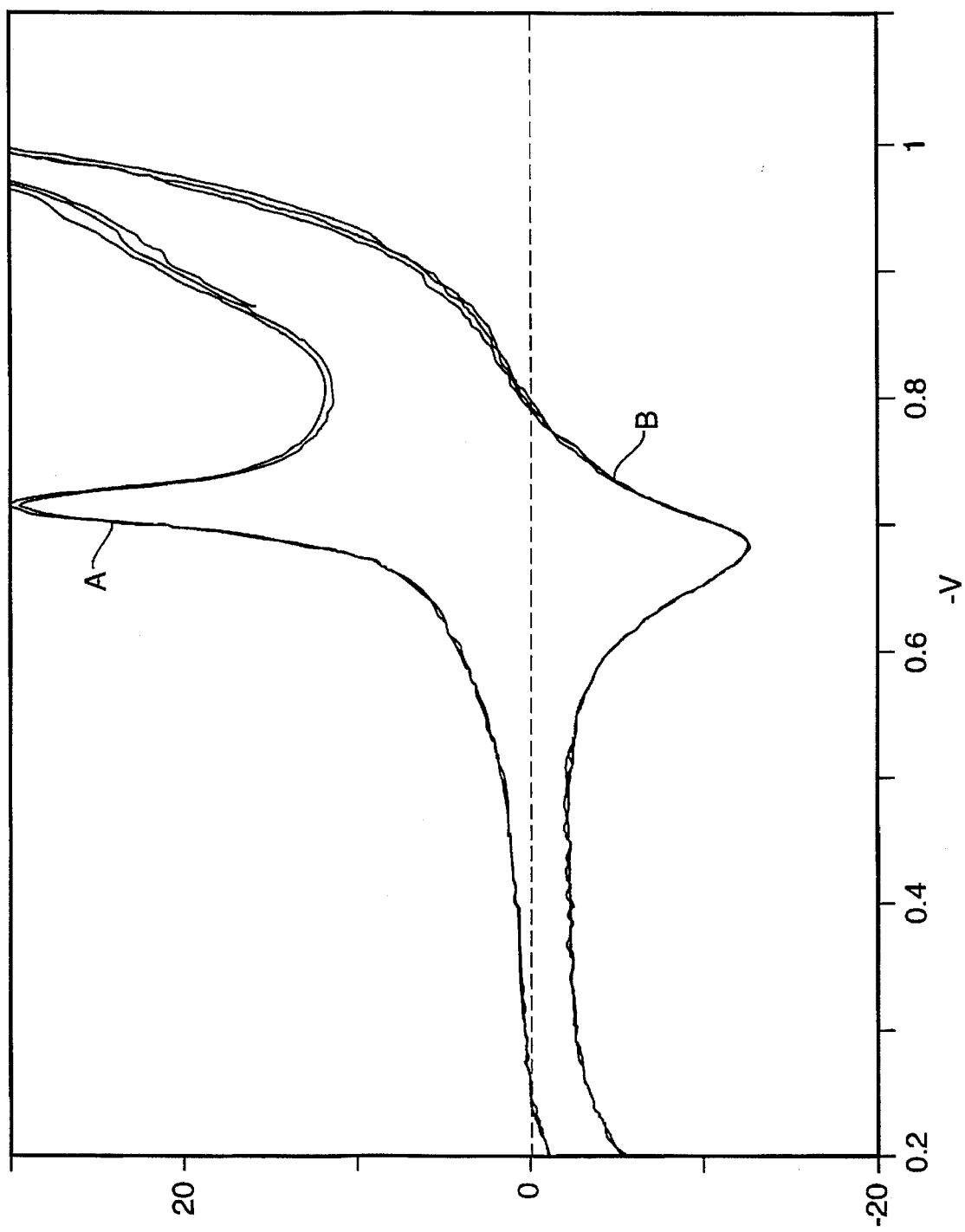
FIG. 2 is a voltammogram illustrating repeated scans indicating the voltammetrically controlled adsorption and desorption of a monolayer onto a substrate.

The working electrode, substrate, and the solution added were the same as described in Example 1. After setting the voltage at $-1.10$ V to clean the substrate, the voltage was scanned linearly from 0.00 V to $-1.10$ V, and back, and then repeated twice. FIG. 2 is the resulting voltammogram.

The peak in Curve A between $-0.70$ and $-0.80$ V represents the desorption of the thiolate layer, while the peak in Curve B represents the oxidative adsorption of the monolayer. The reproducibility of the process is evident from the agreement between the duplicate scans.

EXAMPLE 3

This Example shows the formation of a HOCH$_2$CH$_2$S$^-$ layer on a Au/mica substrate.

The solution used was as described in Example 1. The voltage was scanned linearly from $-0.40$ V to $-1.40$ V and back, and then repeated.

Figure 3:
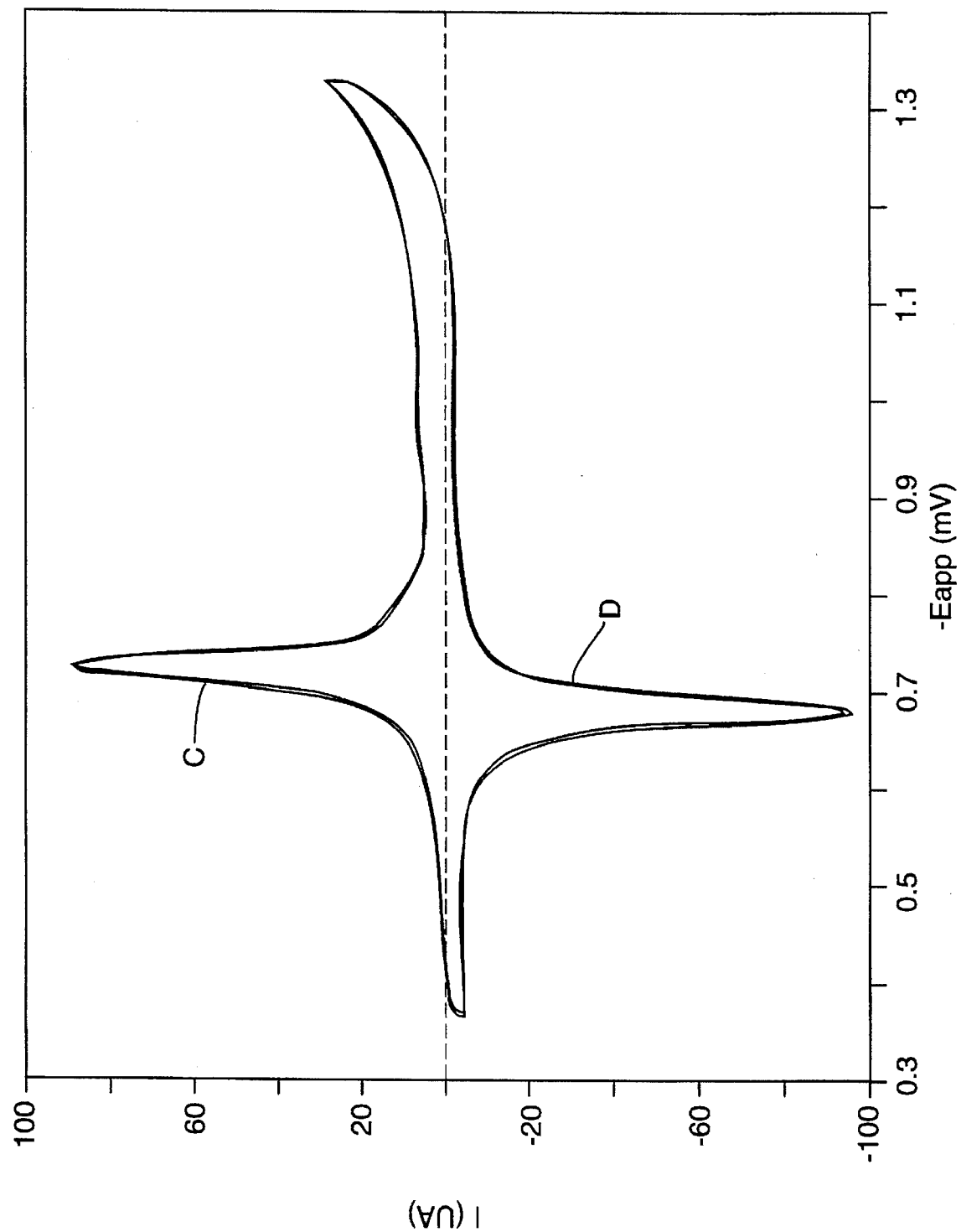
FIG. 3 is a voltammogram showing voltammetrically controlled adsorption and desorption of $HOCH_2CH_2S^-$ on a Au substrate on a mica support.

FIG. 3 shows the voltammogram in which Curve C shows the reductive desorption of the thiolate layer, while Curve D shows the oxidative adsorption onto the substrate. As can be seen, the waves have good definition, and good reproducibility of the process is evident.

EXAMPLE 4

This Example shows the deposition of an ethanethiolate monolayer onto a substrate using ethanol as the electrolytic medium.

The substrate was Au/mica as described in Example 3. The solution used included 10 mM ethanethiol and 0.5M KOH in ethanol. The voltage was scanned linearly from $-0.60$ V to $-1.30$ V, and back, and then repeated. The cell was disconnected from the potentiostat between runs.

Figure 4:
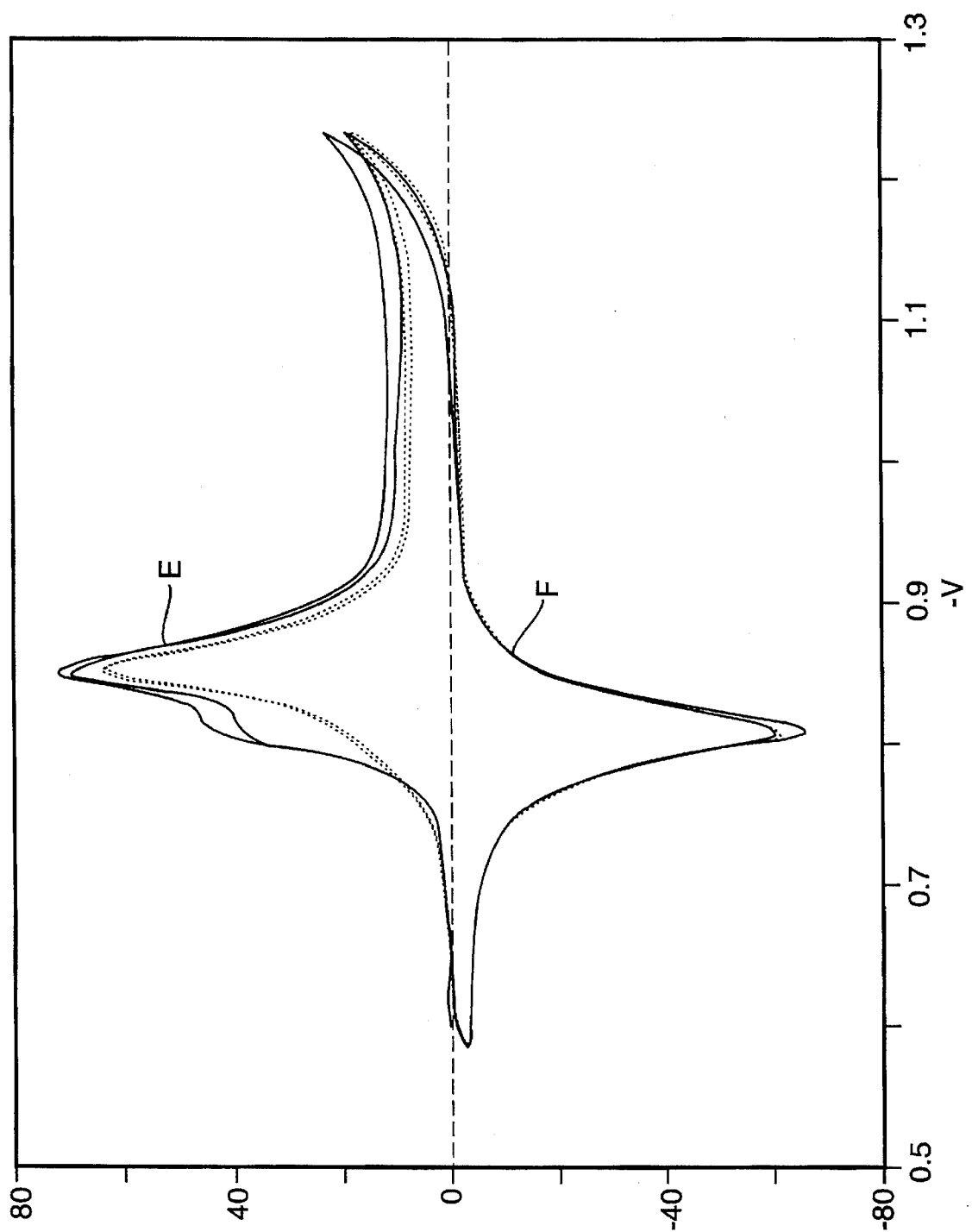
FIG. 4 is a voltammogram illustrating voltammetrically controlled adsorption and desorption in ethanolic KOH of ethanethiolate upon a substrate.

FIG. 4 is the voltammogram which resulted; Curve E shows the reductive desorption and Curve F shows the oxidative adsorption. The first scan or cycle is shown as a solid line, while the dotted line represents the second cycle for each run. Two runs were made on this spot.

While not providing the reproducibility level demonstrated in the prior Examples in water, this Example shows the general nature of the adsorption/desorption reaction for ethanethiolate in ethanol. Improved reproducibility using ethanol can be obtained, as shown in subsequent Examples.

EXAMPLE 5

This Example shows the formation of a hexanethiolate layer on a substrate.

Figure 5:
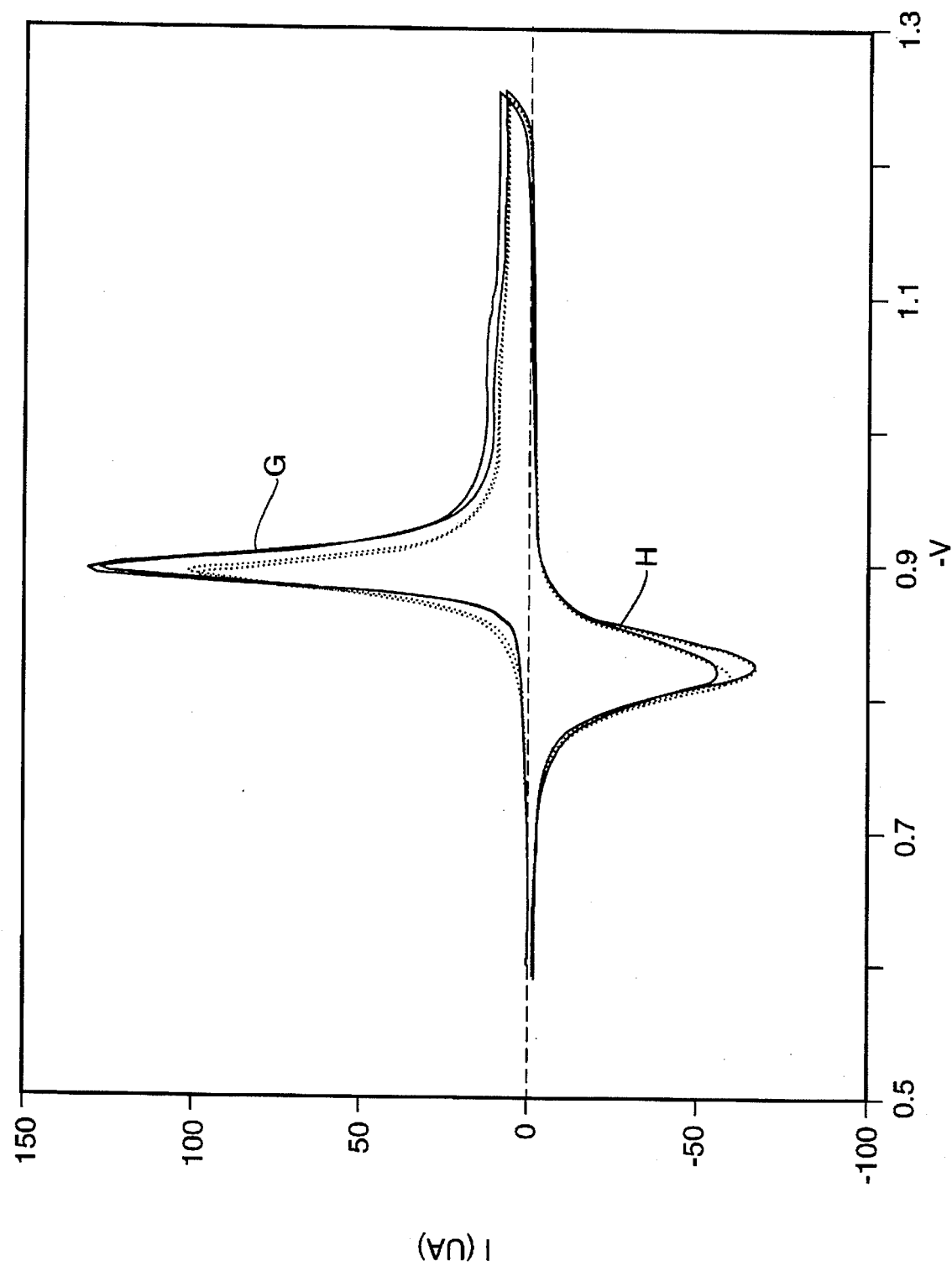
FIGS. 5–7 are voltammograms similar to FIG. 4, except illustrating, respectively, the voltammetrically controlled adsorption-desorption in ethanolic KOH of a monolayer of $C_3(C_2)_5SH$, $CH_3(CH_2)_9SH$, and $CH_3(CH_2)_{15}SH$ upon a substrate.

This Example duplicates Example 4, except using hexanethiol; and the applied voltage was maintained at −0.60 V between runs. FIG. 5 shows the resulting voltammograms, with Curve G showing the reductive desorption and Curve H showing the oxidative adsorption. As can be seen, good reproducibility resulted. In addition, the agreement between the reductive desorption curves (G) for the two runs made on this spot shows that the electrodeposited layer from the second run and the layer that self-assembled during the inert gas purge prior to the first run are similar.

EXAMPLE 6

This Example shows the formation of a decanethiolate layer.

Figure 6:
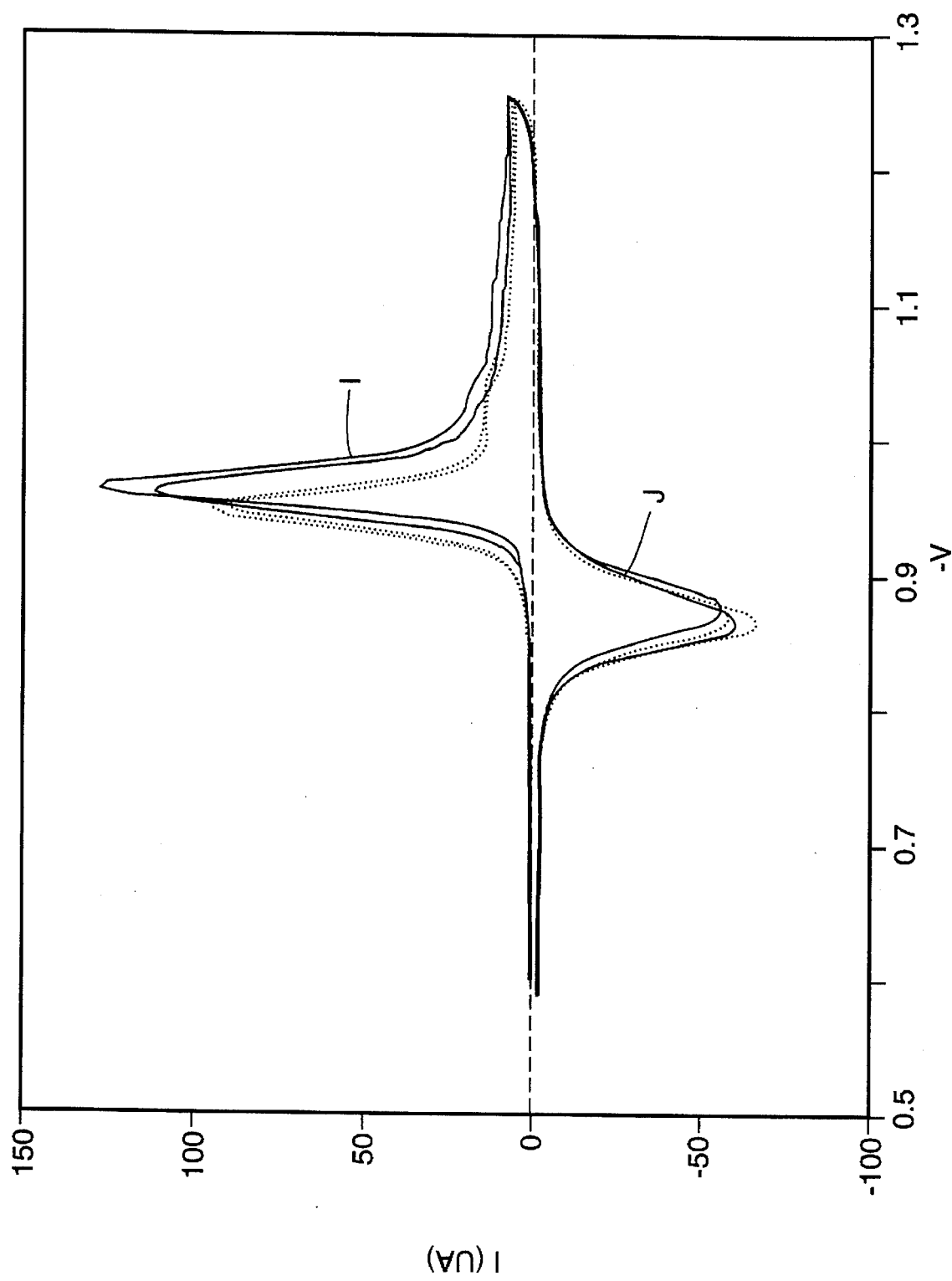

This Example repeats Example 5, except using decanethiol. FIG. 6 shows the resulting scans in which Curve I shows the reductive desorption while Curve J shows the oxidative adsorption.

EXAMPLE 7

This Example shows the formation of a hexadecanethiolate layer.

Figure 7:
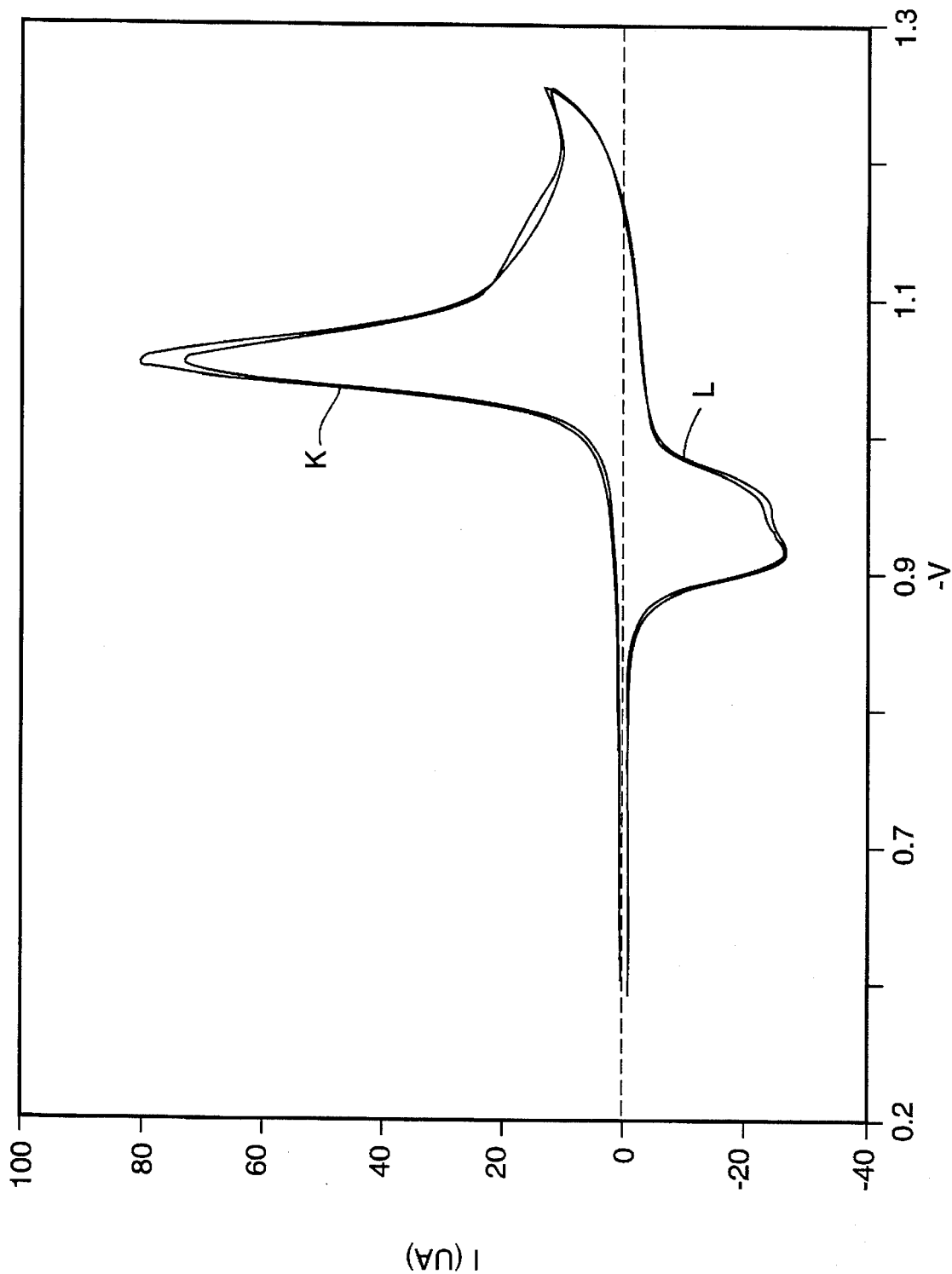

The procedure of Example 4 was repeated, except using hexadecanethiol. Only one scan was made for each run. FIG. 7 shows the resulting scans with Curve K showing the reductive desorption while Curve L shows the oxidative adsorption.

EXAMPLE 8

This Example demonstrates coverage control of the thiolate layer by applying a preselected, constant applied voltage so that the thermodynamics of the system control the extent of coverage of the monolayer formed.

The substrate or working electrode was Au/mica, and the solution used was 10 mM hexanethiol in 0.5M KOH in ethanol. The procedure utilized was to set the voltage at −1.00 V for 30 seconds to clean the electrode. The voltage was then stepped to the designated voltages of −0.95 V, −0.94 V and −0.93 V for 1 minute. A negative voltage scan was started at each designated voltage. The scan direction was reversed at −1.20 V, and the positive scan was then stopped at −0.60 V. The procedure was repeated twice at each voltage.

Figure 8:
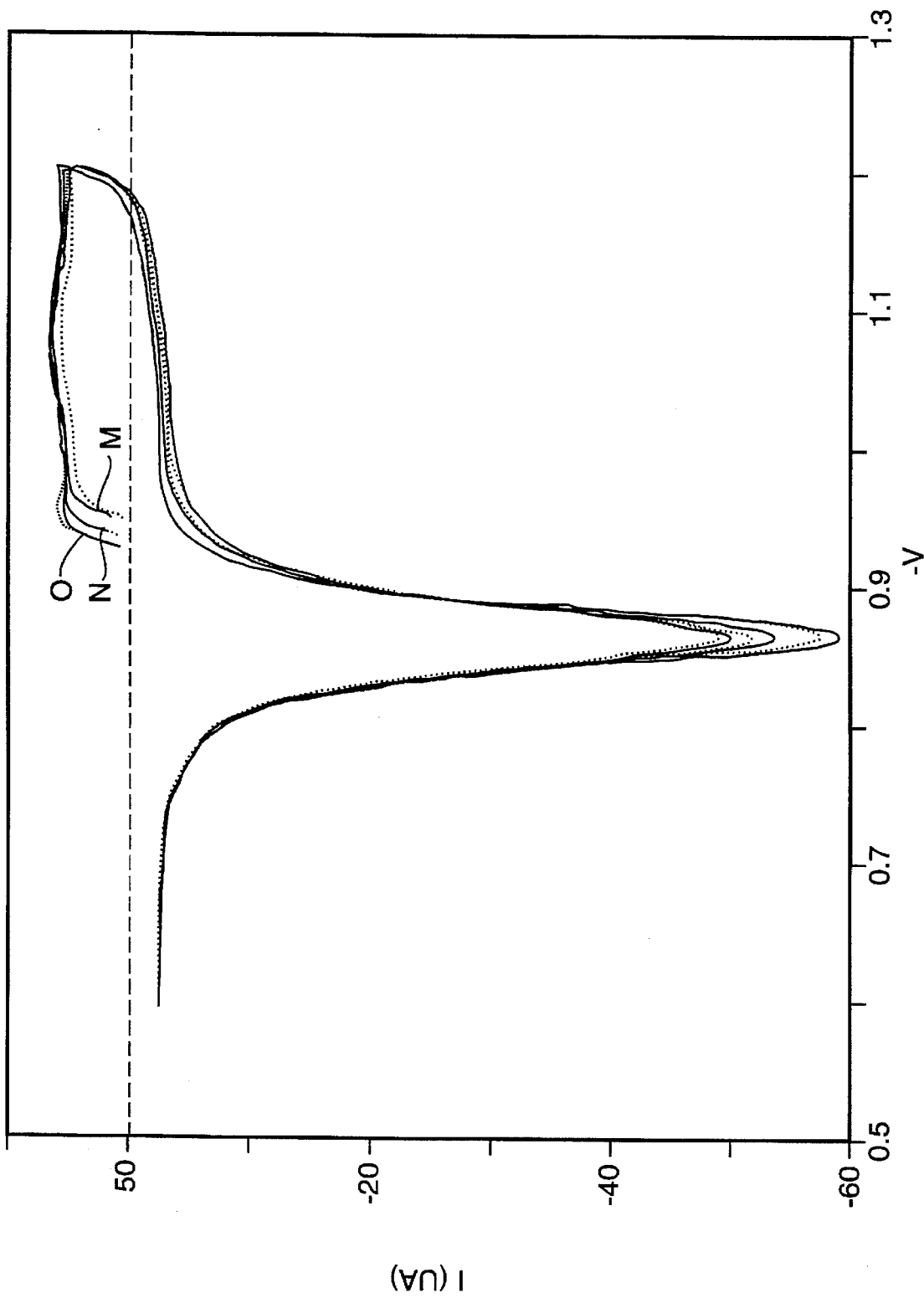
FIG. 8 is a voltammogram showing the effects of thermodynamic control when the adsorption is initiated by using constant applied voltages of −0.95, −0.94 and −0.93 volts producing very low coverages in this case.

FIG. 8 shows the voltammograms in which Curve M represents the scans at −0.95 V, Curve N the scans for −0.94 V and Curve O the scans for −0.93 V. As can be seen, at these applied voltages, coverage is very low, indicating that the applied voltage is preventing deposition. The reproducibility is evident.

EXAMPLE 9

Figure 9:
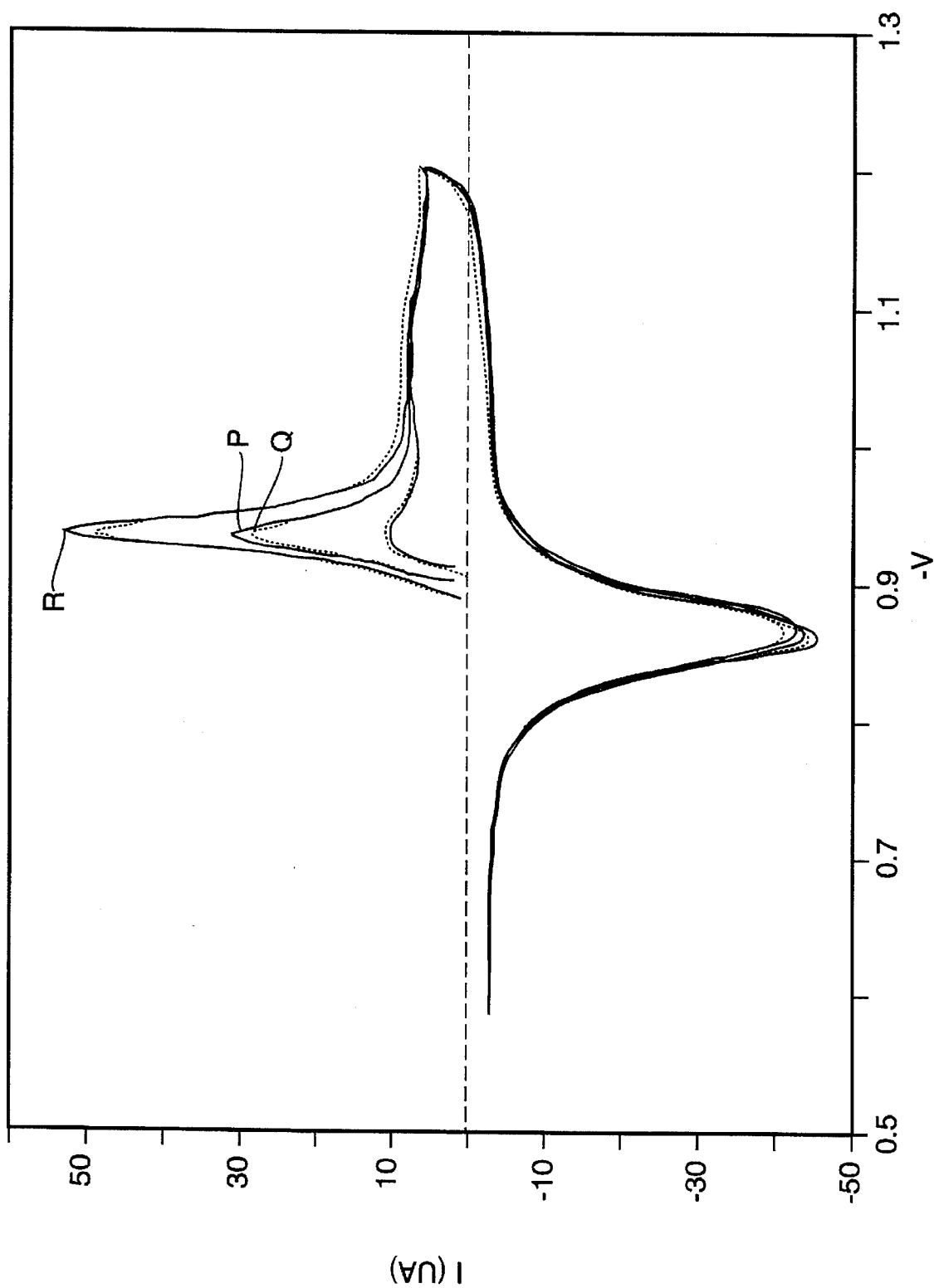
FIG. 9 is a voltammogram similar to FIG. 8, except showing the results of thermodynamic control using constant applied voltages of −0.89, −0.90 and −0.91 volts producing intermediate coverages in this case.

This Example repeats Example 8, except using constant applied voltages of −0.91 V, −0.90 V, and −0.89 V. FIG. 9 is the voltammogram showing the results, with Curves P, Q and R showing, respectively, the scans for −0.91 V, −0.90 V, and −0.89 V.

This Example demonstrates the ability to thermodynamically control deposition producing intermediate coverages from about 10% to about 50% of a monolayer. Again, reproducibility is evident.

EXAMPLE 10

Figure 10:
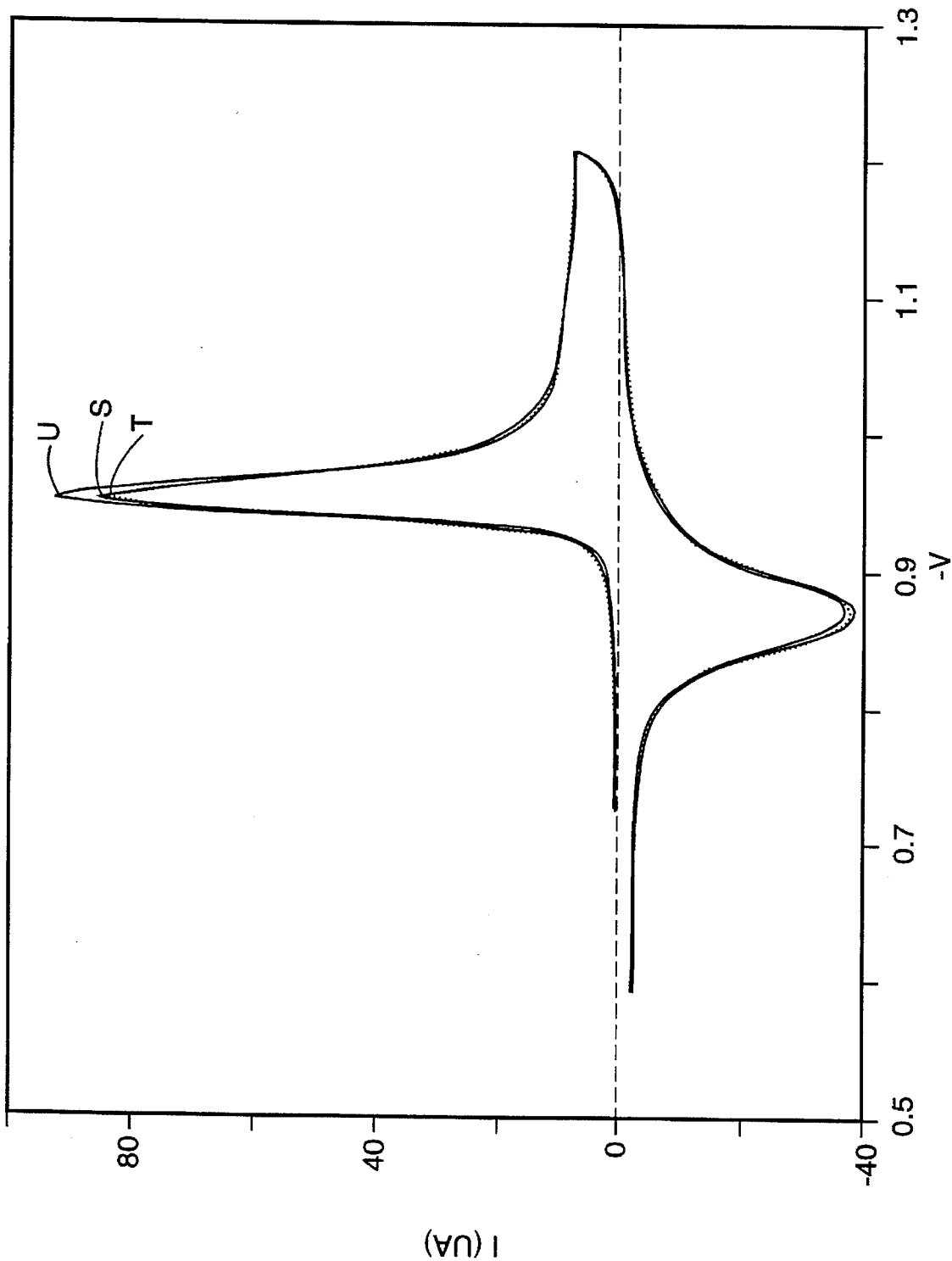
FIG. 10 is a voltammogram similar to FIG. 8, except showing similar control using constant applied voltages of −0.80, −0.79 and −0.73 volts producing nearly complete monolayer coverage in this case.

Example 9 was repeated, except using constant applied voltages of −0.80 V, −0.79 V and −0.73 V. FIG. 10 shows the resulting voltammograms, with Curve S, Curve T and Curve U, respectively, representing the scans for −0.80 V, −0.79 V, and −0.73 V. In this case, Curves S and T are almost identical and therefore difficult to distinguish.

This Example demonstrates deposition control for higher coverages that are near, but still less than, a full monolayer. Reproducibility is still evident.

EXAMPLE 11

This Example shows the deposition of a $CF_3(CF_2)_7(CH_2)_2S^-$ monolayer.

Figure 11:
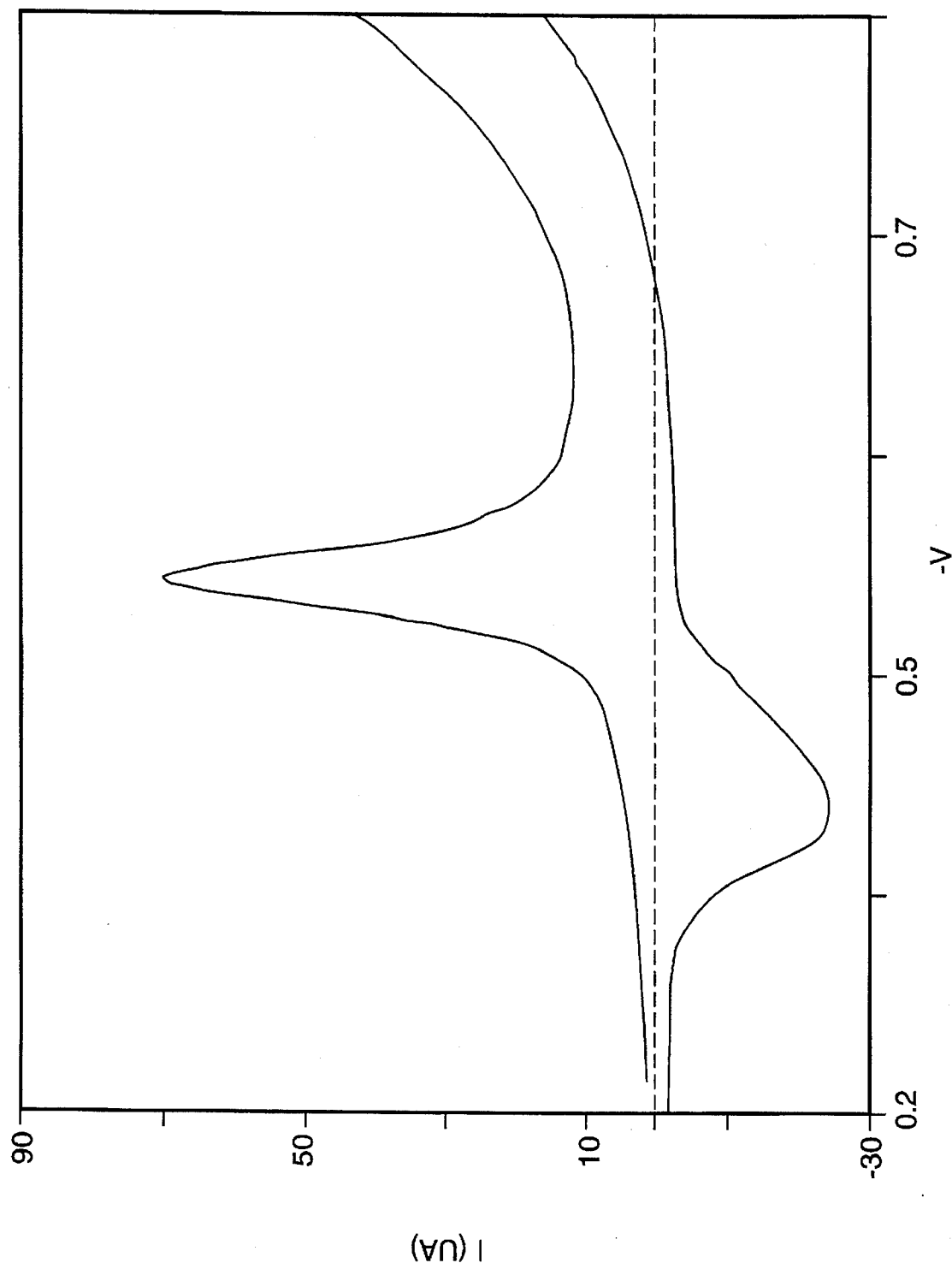
FIG. 11 is a voltammogram illustrating the voltammetrically controlled adsorption-desorption when using $CF_3(CF_2)_7(CH_2)_2SH$.

The procedure used was as set forth in Example 4, except that a platinum wire pseudo-reference was used, and only one voltage scan was made. FIG. 11 shows the resulting voltammogram.

EXAMPLE 12

This Example shows the formation of a partial monolayer of $COOH(CH_2)S^-$ on a substrate.

Figure 12:
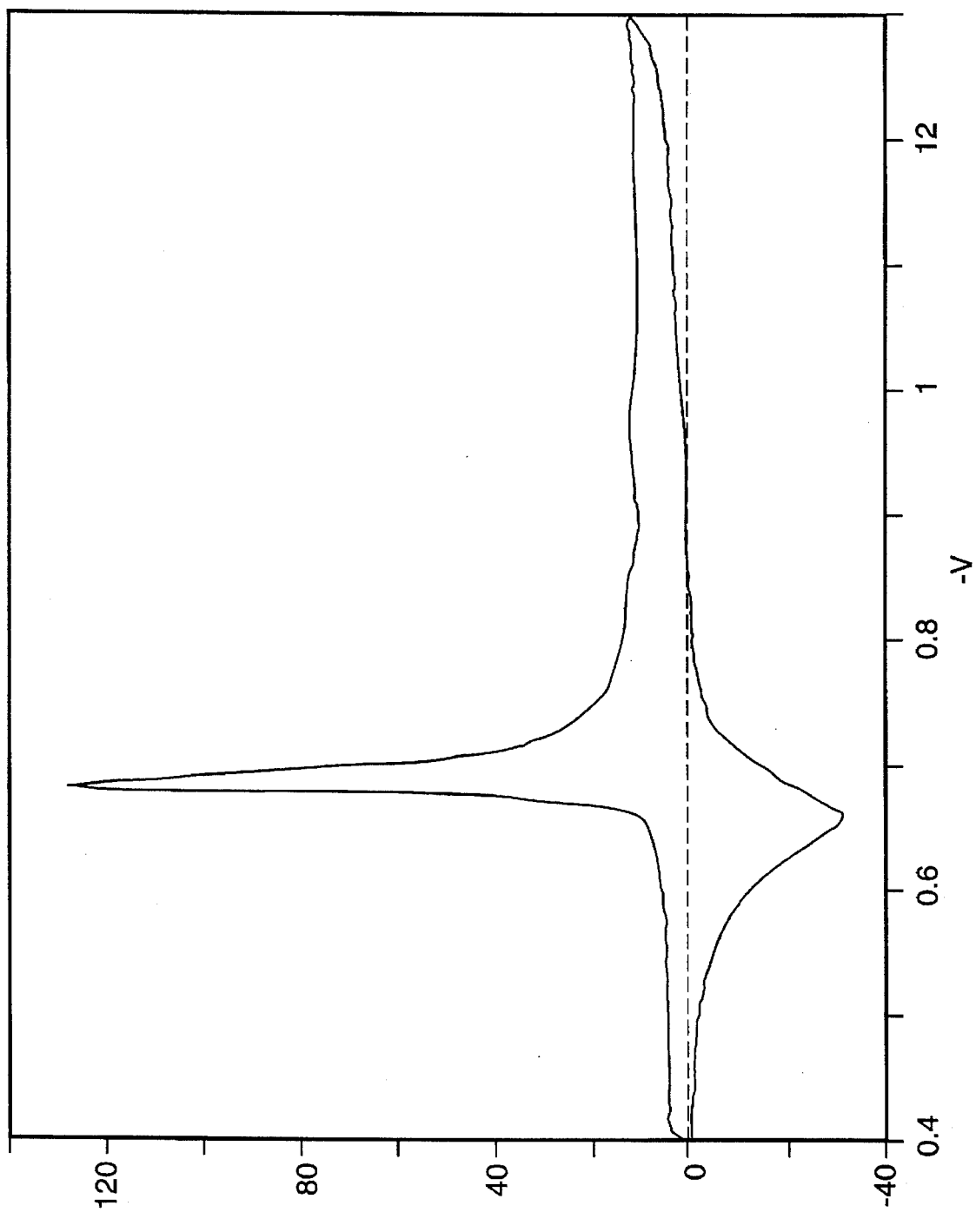
FIG. 12 is a voltammogram showing the use of $COOH(CH_2)SH$ in the voltammetrically controlled adsorption-desorption.

The procedure was as set forth in Example 3. FIG. 12 shows the resulting voltammogram.

EXAMPLE 13

Figure 13:
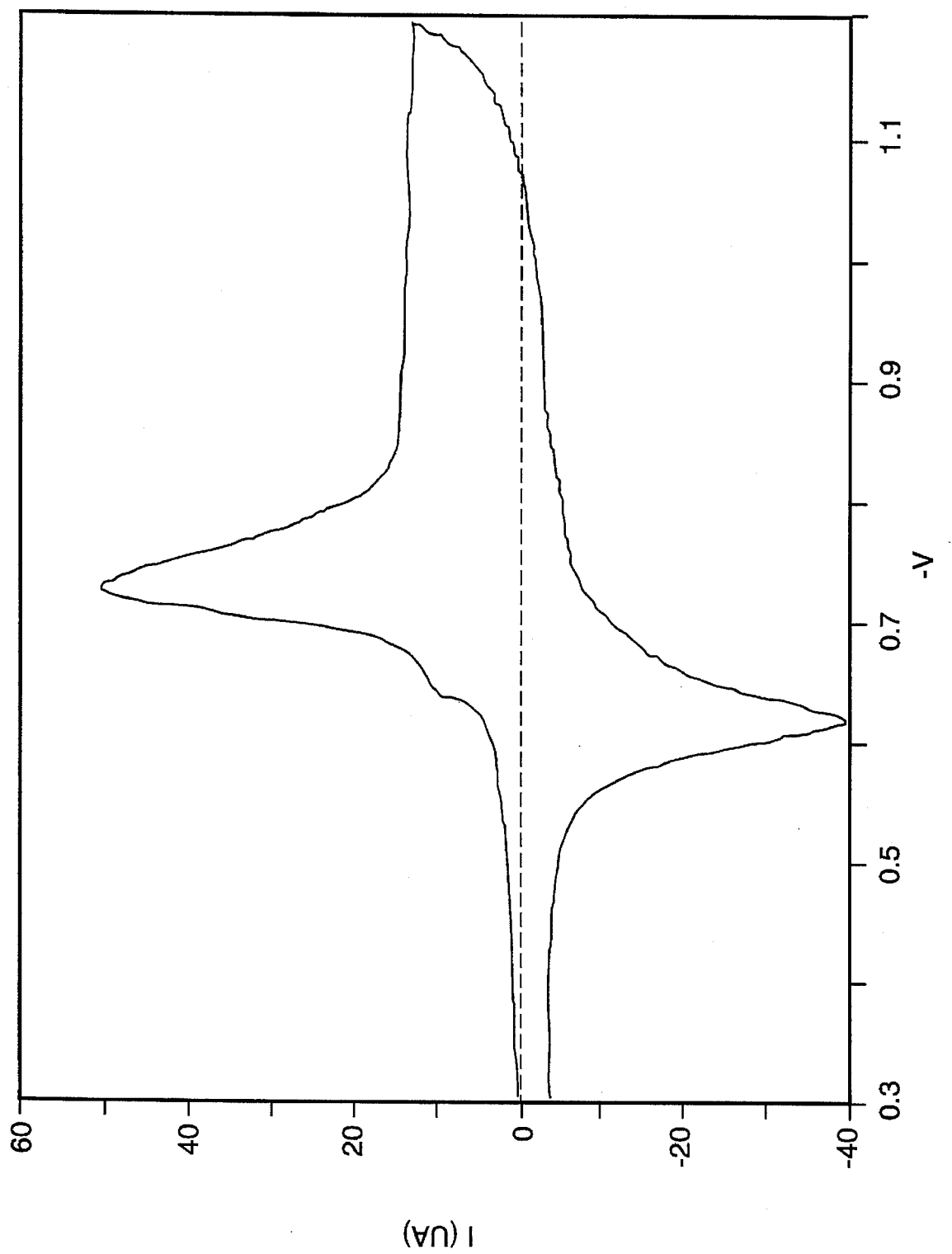
FIG. 13 is a voltammogram showing the use of a sulfidophenyl moiety in the voltammetrically controlled adsorption-desorption.

This Example shows the formation of a partial monolayer of sulfidophenyl on a substrate. The procedure was as set forth in Example 3, except that a platinum wire pseudo-reference was used, and only one voltage scan was made. FIG. 13 shows the resulting voltammogram.

Thus, as has been seen, the present invention provides a facile process for forming a thiolate partial monolayer of a predictable level of coverage which has excellent reproducibility. This process is thermodynamically controlled, so that, by selecting a predetermined voltage that is constantly applied for a period of time to establish the redox equilibrium, the desired level of coverage of a wide variety of thiolates can be deposited.

We claim:

1. A method for forming a partial monomolecular layer of a thiolate having the formula, $XRS^-$, wherein R is a member selected from the group consisting of linear chain hydrocarbons, branched chain hydrocarbons and aromatics, and X is a member selected from the group consisting of OH, COOH, $CH_3$, $CF_3(CF_2)_7$, inorganic complexes with thiol ligands, organometallic compounds, cyclodextrins, and crown ethers, upon a substrate, which comprises determining the constant voltage necessary to be applied to provide a desired extent of coverage of said thiolate upon said substrate, providing an electrochemical system for forming said thiolate partial monomolecular layer upon said substrate and applying said constant voltage for a time sufficient to establish a redox equilibrium, which deposits the thiolate partial monomolecular layer upon said substrate.

2. The method of claim 1 wherein said substrate is gold.

3. The method of claim 1 wherein, before said constant voltage is applied, said electrochemical system is subjected to a voltage selected to clean the substrate to be covered.

4. The method of claim 1 wherein X is $CH_3$.

5. The method of claim 1 wherein X is OH.

6. The method of claim 1 wherein X is COOH.

7. The method of claim 1 wherein X is $CF_3(CF_2)_7$.

8. The method of claim 1 wherein R is $(CH_2)_n$ and n is an integer of 1 or more.

9. The method of claim 1 wherein R is phenyl.

10. The method of claim 1 wherein X is $CH_3$ and n is 5.

11. The method of claim 1 wherein said electrochemical system includes an Ag/AgCl reference electrode, a platinum counter electrode and ethanolic KOH as the electrolytic solution.

12. The method of claim 1 wherein said electrolytic solution includes KOH as the electrolyte.

13. The method of claim 1 wherein said thiolate is present in an amount of at least about 1 mM.

14. The method of claim 1 wherein said constant voltage is determined using a negative linear voltage sweep.

* * * * *

UNITED STATES PATENT AND TRADEMARK OFFICE
CERTIFICATE OF CORRECTION

PATENT NO.   :   5,635,047

DATED        :   June 3, 1997

INVENTOR(S)  :   Porter et al.

It is certified that error appears in the above-identified patent and that said Letters Patent is hereby corrected as shown below:

In Column 3, line 42: "$C_3(C_2)_5SH$" should read -- $CH_3(CH_2)_5SH$ --.

Signed and Sealed this

Fourth Day of November, 1997

BRUCE LEHMAN

*Attest:*

*Attesting Officer*          *Commissioner of Patents and Trademarks*

UNITED STATES PATENT AND TRADEMARK OFFICE
CERTIFICATE OF CORRECTION

PATENT NO.    :   5,635,047
DATED         :   June 3, 1997
INVENTOR(S)   :   Porter et al.

It is certified that error appears in the above-identified patent and that said Letters Patent is hereby corrected as shown below:

Column 1, lines 7-11: "The United States government has certain rights in this invention pursuant to Contract No. W-7405-Eng-82 (DOE-ISU) and Contract No. ITA81-02 between the U.S. National Aeronautic and Space Administration and Iowa State University." should read --- The United States Government has certain rights in this invention. This invention was made with government support pursuant to Contract No. W-7405-Eng-82 between the U.S. Department of Energy and Iowa State University, Contract No. ITA87-02 between the U.S. Department of Commerce and Iowa State University, and Grant Numbers NAS7-918 and JPL959452 awarded by NASA. ---

Signed and Sealed this

Thirtieth Day of December, 1997

Attest:

BRUCE LEHMAN

*Attesting Officer*          *Commissioner of Patents and Trademarks*